United States Patent
Benkovic et al.

(10) Patent No.: US 9,562,250 B2
(45) Date of Patent: *Feb. 7, 2017

(54) METHODS FOR NUCLEIC ACID MANIPULATION

(71) Applicant: THE PENN STATE RESEARCH FOUNDATION, University Park, PA (US)

(72) Inventors: Stephen J Benkovic, State College, PA (US); Frank Salinas, Wheaton, IL (US)

(73) Assignee: The Penn State Research Foundation, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/313,193

(22) Filed: Jun. 24, 2014

(65) Prior Publication Data

US 2014/0356936 A1    Dec. 4, 2014

Related U.S. Application Data

(63) Continuation of application No. 14/268,444, filed on May 2, 2014, now Pat. No. 9,322,058, which is a (Continued)

(51) Int. Cl.
C12Q 1/68 (2006.01)
C12P 19/34 (2006.01)
(Continued)

(52) U.S. Cl.
CPC .......... *C12P 19/34* (2013.01); *C12N 15/1027* (2013.01); *C12Q 1/686* (2013.01); *C12Q 1/6806* (2013.01); *C12Q 1/6844* (2013.01)

(58) Field of Classification Search
CPC ............ C12Q 1/6844; C12Q 2521/507; C12Q 2521/513; C12Q 2527/125; C12Q 1/6806; C12Q 1/686; C12N 15/1027; C12P 19/34
See application file for complete search history.

(56) References Cited

U.S. PATENT DOCUMENTS 5,223,414 A    6/1993 Zarling et al.
5,616,478 A    4/1997 Chetverin et al.
(Continued)

FOREIGN PATENT DOCUMENTS

CN        1489632 A       4/2004
WO    WO-94/03624       2/1994
(Continued)

OTHER PUBLICATIONS

Cheng, et al., "Effective Amplification of Long Targets from Cloned Inserts and Human Genomic DNA", Proc. Natl.Acad.Sci. 91, 5695-5699 (1994).
(Continued)

*Primary Examiner* — Teresa Strzelecka
(74) *Attorney, Agent, or Firm* — Husch Blackwell LLP

(57) ABSTRACT

A method for replicating and amplifying a target nucleic acid sequence is described. A method of the invention involves the formation of a recombination intermediate without the prior denaturing of a nucleic acid duplex through the use of a recombination factor. The recombination intermediate is treated with a high fidelity polymerase to permit the replication and amplification of the target nucleic acid sequence. In preferred embodiments, the polymerase comprises a polymerase holoenzyme. In further preferred embodiments, the recombination factor is bacteriophage T4 UvsX protein or homologs from other species, and the polymerase holoenzyme comprises a polymerase enzyme, a clamp protein and a clamp loader protein, derived from viral, bacteriophage, prokaryotic, archaebacterial, or eukaryotic systems.

13 Claims, 3 Drawing Sheets

Related U.S. Application Data continuation of application No. 13/722,765, filed on Dec. 20, 2012, now Pat. No. 8,759,000, which is a continuation of application No. 12/786,053, filed on May 24, 2010, now Pat. No. 8,361,718, which is a continuation of application No. 11/204,125, filed on Aug. 15, 2005, now Pat. No. 7,723,031, which is a continuation of application No. 10/125,973, filed on Apr. 19, 2002, now Pat. No. 6,929,915.

(60) Provisional application No. 60/285,127, filed on Apr. 20, 2001.

(51) Int. Cl.
*C12N 15/10* (2006.01)
*C07H 21/02* (2006.01)

(56) References Cited

U.S. PATENT DOCUMENTS

| | | | |
|---|---|---|---|
| 5,668,004 | A | 9/1997 | O'Donnell ............ 435/91.2 |
| 5,670,316 | A | 9/1997 | Sena et al. |
| 5,670,325 | A | 9/1997 | Lapidus et al. |
| 5,928,870 | A | 7/1999 | Lapidus et al. |
| 5,945,312 | A | 8/1999 | Goodman et al. ......... 435/91.2 |
| 5,945,339 | A | 8/1999 | Holloman et al. |
| 5,958,698 | A | 9/1999 | Chetverin et al. |
| 6,001,568 | A | 12/1999 | Chetverin et al. |
| 6,033,881 | A | 3/2000 | Himmler et al. |
| 6,074,853 | A | 6/2000 | Pati et al. |
| 6,306,590 | B1 | 10/2001 | Mehta et al. |
| 6,432,360 | B1 | 8/2002 | Church |
| 6,440,706 | B1 | 8/2002 | Vogelstein et al. |
| 6,699,693 | B1 | 3/2004 | Marians et al. .......... 435/91.2 |
| 6,929,915 | B2 | 8/2005 | Benkovic et al. |
| 7,723,031 | B2 | 5/2010 | Benkovic et al. |
| 7,785,790 | B1 | 8/2010 | Church et al. |
| 7,820,413 | B2 | 10/2010 | Benkovic et al. |
| 7,824,889 | B2 | 11/2010 | Vogelstein et al. |
| 7,906,279 | B2 | 3/2011 | Benkovic et al. |
| 7,915,015 | B2 | 3/2011 | Vogelstein et al. |
| 7,985,565 | B2 | 7/2011 | Mayer et al. |
| 8,124,342 | B2 | 2/2012 | Benkovic et al. |
| 8,129,116 | B2 | 3/2012 | Benkovic et al. |
| 8,137,913 | B2 | 3/2012 | Benkovic et al. |
| 8,143,008 | B2 | 3/2012 | Kawashima et al. |
| 8,241,851 | B2 | 8/2012 | Benkovic et al. |
| 8,361,718 | B2 | 1/2013 | Benkovic et al. |
| 8,389,216 | B2 | 3/2013 | Benkovic et al. |
| 8,652,810 | B2 | 2/2014 | Adessi et al. |
| 8,673,561 | B2 | 3/2014 | Benkovic et al. |
| 8,759,000 | B2 | 6/2014 | Benkovic et al. |
| 8,765,374 | B2 | 7/2014 | Benkovic et al. |
| 2003/0143525 | A1 | 7/2003 | Benkovic et al. |
| 2003/0219792 | A1 | 11/2003 | Armes et al. |
| 2004/0171060 | A1 | 9/2004 | Benkovic et al. |
| 2005/0100900 | A1 | 5/2005 | Kawashima et al. |
| 2005/0112631 | A1 | 5/2005 | Piepenburg et al. |
| 2009/0017462 | A1* | 1/2009 | Piepenburg et al. ............ 435/6 |
| 2010/0279358 | A1 | 11/2010 | Benkovic et al. |
| 2010/0285482 | A1 | 11/2010 | Benkovic et al. |
| 2014/0228254 | A1 | 8/2014 | Adessi et al. |

FOREIGN PATENT DOCUMENTS

| | | |
|---|---|---|
| WO | WO-98/08975 | 3/1998 |
| WO | WO-98/44151 | 10/1998 |
| WO | WO-00/18957 | 4/2000 |
| WO | WO-00/47767 | 8/2000 |
| WO | WO-00/060919 | 10/2000 |
| WO | WO-00/60919 | 10/2000 |
| WO | WO-01/81908 | 11/2001 |
| WO | WO-02/46456 | 6/2002 |
| WO | WO-02/072772 | 9/2002 |

OTHER PUBLICATIONS

Ling, L.L. Kenhavong, P., Dias, C., and Thilly, W.G. "Optimization of the Ploymerase Chain Reaction With Regard to Fidelity; Modified T7, Taq, and Vent DNA Polymerases", PCR Methods Appl. 1(1) pp. 63-69 (1991).

Cariello, N.F., Swedenberg, J.A. and Skopek, T.R., "Fidelity of Thermococcus Litoralis, DNA Polymerase (Vent) in PCR Determined by Denaturing Gradient Gel Electrophoresis", Nucleic Acids Res. 19(15), pp. 4193-4198 (1991).

Lundberg, K.S., Shoemaker, D.D., Adams, M.W., Short, J.M. Sorge, J.A., and Mather, E.J., "High-fidelity Amplification Using a Thermostable DNA Polymerase Isolated From Pyrococcus Furiosus", Gene 108(1), pp. 1-6 (1991).

Barnes, W.M., "The Fidelity of Taq Polymerase Catalyzing PCR is Improved by an N-terminal Deletion", Gene 112(1), pp. 29-35 (1992).

Matilla, P., Korpela, J., Tenkanen, T., and Pitkanen, K., "Fidelity of DNA Synthesis by the Thermococcus Litorialis DNA Polymerase—An Extremely Heat Stable Enzyme with Proofreading Activity", Nucleic Acids Res. 19(18), pp. 4967-4973 (1991).

Morrical,S., et al., "Amplification of Snap-back DNA Synthesis Reactions by the uvsX Recombinase of Bacteriophage T4", Journal of Biological Chemistry, 266(21)14031-14308(1991).

Beemink et al., *Trends in Bio. Sci.* (Oct. 1999) 385-389.

Benkovic et al., *Annu. Rev. Biochem.* (2001) 70:181-208.

Formosa et al., *Cell* (Dec. 5, 1986) 47:793-806.

Harris et al., *J. Mol.Biol.* (1989) 206:19-27.

Jiang et al., Biochem: Biophys. Res. Commun. (Feb. 24, 1997)231(3):600-6005.

Nishinaka et al., *Pro.Nat.Acad.Sci.*, USA (Sep. 1998)95:11071-11076.

Podust et al., Biochem. (1995)5003-5010.

Salinas et al., Biochem.Biophys.Res.Commun. (Dec. 15, 1994)205(2):1004-1009.

Salinas et al., Cell (Jul. 14, 1995) 82(1):111-119.

Salinas et al., *J. Biol Chem*. (Mar. 10, 1995)270(10):5181-5186.

Salinas, PhD Thesis 1997.

Listed articles in Google search: Clerget et al., "Phage HK022 Roi Protein Inhibits Phage Lytic Growth in *Escherichia coli* Integratin Host Factor Mutants", Journ. of Bacterio, vol. 178, No. 14, p. 4077-4083 (Jul. 1996).

New England Biolabs Online Catalog, T4 DNA Polymerase, p. 1 (www.neb.com/nebecomm/products/product_M0203.asp), 2008.

Morrical, S.W. et al., "The UvsX Protein of Bacteriophage T4 Modulates Recombination-dependent DNA synthesis in Vitro," J. Biol. Chem., vol.265, pp. 15096-15103 (1990).

Eggleston, A.K, et al., "An overview of homologous pairing and DNA strand exchange proteins," Biochimie, vol. 73, pp. 163-176 (1991).

"Summary Table," Trends in Biochemical Sciences, vol. 25, p. 206 (Apr. 2000).

Barry et al., "A Role for Two DNA Hellcases in the Replication of T4 Bacteriophage DNA", *J. Biol. Chem.*, 269(52), 33063-33068 (1994).

Adessi, C, et al, "Solid Phase DNA Amplification: characterisation of primer attachment and amplification mechanisms ," Nucleic Acids Research, vol. 28, No. 20, e87, 1-8, 2000.

Andreadis, Joanne D., et al, "Use of immobilized PCR primers to generate covalently immobilized DNAs for in vitro transcription/translation reactions," Nucleic Acids Research, e5, 2000.

Belanger, Karyn, et al, "Bacteriophage T4 Initiates Bidirectional DNA Replication through a Two-Step Process," Molecular Cell, 693-701, 1998.

Bing, David, et al, "Bridge Amplification: A Solid Phase PCR System for the Amplification and Detection of Allelic Differences in Single Copy Genes," Genetic Identity Conference Proceedings, Seventh International Symposium on Human Identification, 1996.

Borer, Philip N., et al, "Stability of Ribonucleic acid Double-stranded Helices," J. Mol. Biol., 843-853, 1974.

Chetverin, Alexander, etal, "Oligonucleotide Arrays: New Concepts and Possibilities," Bio/Technology, 1093-1099, Nov. 12, 1994.

(56) References Cited

OTHER PUBLICATIONS

Abrams, Ezra, et al, "Bridge Amplification for DNA-based Diagnostics," Chapter 1.9, 171-189, Mosaic Technologies, Boston University, Speaker at the Diagnostic Gene Detection and Quantification Technologies Conference, 1997.

Dubiley, Svetlana, et al, "Polymorphism analysis and gene detection by minisequencing on an array of gel-immobilized primers," e19, Nucleic Acids Research,1999, vol. 27, No. 18, Oxford University Press.

Formosa, Timothy, et al, "DNA Synthesis Dependent on Genetic Recombination: Characterization of a Reaction Catalyzed by Purified Bacteriophage T4 Proteins," Cell vol. 47, 793-806, Dec. 5, 1986, Cell Press.

Mitra, Robi, et al, "In situ localized amplification and contact replication of many individual DNA molecules," e34, Nucleic Acids Research, 1999, vol. 27, No. 24, pp. i-vi, Oxford University Press.

Morrical, Scott, et al, "Amplification of Snap-back DNA Synthesis Reactions by the uvsX Recombinase of Bacteriophage T4," Journal of Biological Chemistry, vol. 286, No. 21 Jul. 25 Issue, pp. 14031-14038, 1991, The American Society for Biochemistry and Molecular Biology, Inc.

Rehman, F., et al, "Immobilization of Acrylamide-modified Oligonucleotides by Co-polymerization," Nucleic Acids Research 1999, vol. 27, No. 2, pp. 649-655, Oxford University Press.

Rychlik, et al, "A computer program for choosing optimal oligonucleotides for filter hybridization, sequencing and in vitro amplification of DNA," Nucleic Acids Research, vol. 17, No. 21, 8543-8551, 1989, IRL Press.

SantaLucia, John, "A unified view of polymer, dumbbell, and oligonucleotide DNA nearest-neighbor thermodynamics," Proc. Natl. Acad. Sci. USA, vol. 95, pp. 1460-1465, Feb. 1998, Biochemistry.

Walker, et al, "Strand displacement amplification—an isothermal, in vitro DNA amplification technique," Nucleic Acids Research, vol. 20, No. 7, pp. 1691-1696, Oxford University Press 1992.

Walter, Nils, et al, "Strand displacement amplification as an in vitro model for rolling-circle replication: Deletion formation and evolution during serial transfer," Proc. Natl. Acad. Sci. USA, vol. 91, pp. 7937-7941, Aug. 1994, Evolution.

Yershov, et al, "DNA Analysis and Diagnostics on Oligonucleotide Microchips," Proc. Natl. Acad. Sci. USA, vol. 93, pp. 4913-4918, May 1996, Genetics.

* cited by examiner

SEQUENCE LISTING

<160> NUMBER OF SEQ ID NOS: 2

<210> SEQ ID NO 1
<211> LENGTH: 30
<212> TYPE: DNA
<213> ORGANISM: Artificial sequence
<220> FEATURE:
<223> OTHER INFORMATION: synthetic sequence

<400> SEQUENCE: 1
tgatacacct attccgggct atacttatat                30

<210> SEQ ID NO 2
<211> LENGTH: 40
<212> TYPE: DNA
<213> ORGANISM: Artificial sequence
<220> FEATURE:
<223> OTHER INFORMATION: synthetic sequence

<400> SEQUENCE: 2
cgctcaatcg tctgaaatgg attatttaca ttggcagatt                40

METHODS FOR NUCLEIC ACID MANIPULATION

CROSS-REFERENCE TO RELATED APPLICATIONS

This is a continuation of U.S. application Ser. No. 14/268,444, filed May 2, 2014, which is a continuation of U.S. application Ser. No. 13/722,765, filed Dec. 20, 2012, which is a continuation of U.S. application Ser. No. 12/786,053, filed May 24, 2010, now U.S. Pat. No. 8,361,718, which is a continuation of U.S. application Ser. No. 11/204,125, filed Aug. 15, 2005, U.S. Pat. No. 7,723,031, which is a continuation of application Ser. No. 10/125,973, filed Apr. 19, 2002, now U.S. Pat. No. 6,929,915, that claims priority of U.S. Provisional Application Ser. No. 60/285,127 filed Apr. 20, 2001, whose disclosures are incorporated herein by reference.

STATEMENT REGARDING FEDERALLY SPONSORED RESEARCH OR DEVELOPMENT

This invention was made with government support under Grant No. GM013306, awarded by The National Institutes of Health. The Government has certain rights in the invention.

REFERENCE TO A MICROFICHE APPENDIX

Not applicable

BACKGROUND OF THE INVENTION

The present invention is directed towards a process for the amplification of a target nucleic acid sequence contained in a larger nucleic acid independent of using a thermocycle or a thermostable polymerase. Unlike current technologies that employ a thermocycle and are therefore dependent upon a thermostable polymerase, the current invention allows for specific primer template association at a low temperature that will remain constant over the duration of the reaction.

A method for the site-specific amplification of a region of nucleic acid is described. Current amplification technology is based upon the Polymerase Chain Reaction (PCR). This PCR system can be thought of as involving three main components. First DNA oligonucleotides complementary to the flanking ends of the target sequence are required. These DNA oligonucleotides serve as primers for the initiation of DNA replication by the second component of the system, a thermostable DNA dependent DNA polymerase, such as the Taq polymerase. The use of a thermostable DNA polymerase is absolutely required in PCR so that the polymerase activity can survive the third component, the thermal cycle. The thermal cycle uses high temperatures, usually 95 degrees Celsius, to melt the target duplex DNA so that a subsequent annealing temperature, usually in the range of 50-60 degrees Celsius, permits the annealing of the primers to the appropriate locations flanking the target DNA. Following the annealing step, the thermal cycle incorporates a polymerization temperature, usually 72 degrees Celsius, which is the optimal temperature of polymerization for the current thermostable polymerases used in PCR.

The requirement of a thermal cycle to facilitate the annealing of the primers flanking the target DNA to be amplified has several drawbacks. Primer annealing temperature is an important parameter in the success of PCR amplification. The annealing temperature is characteristic for each oligonucleotide: it is a function of the length and base composition of the primer as well as the ionic strength of the reaction buffer. The theoretical amplification value is never achieved in practice. Several factors prevent this from occurring, including: competition of complementary daughter strands with primers for reannealing (i.e. two daughter strands reannealing results in no amplification); loss of enzyme activity due to thermal denaturation, especially in the later cycles; even without thermal denaturation, the amount of enzyme becomes limiting due to molar target excess in later cycles (i.e. after 25-30 cycles too many primers need extending); possible second site primer annealing and non-productive priming. Moreover, primers must avoid stretches of polybase sequences (e.g. poly dG) or repeating motifs—these can hybridize with inappropriate register on the template. Inverted repeat sequences should also be avoided so as to prevent formation of secondary structure in the primer, which would prevent hybridization to template.

An additional drawback is the costly need for temperature baths, which are required to shift their temperatures up and down rapidly, and in an automated programmed manner. These are known as thermal cyclers or PCR machines.

A further problem with PCR is the lack of fidelity of the various Polymerases (Table 1) under different conditions. However, with increasing number of cycles the greater the probability of generating various artifacts (e.g. mispriming products). It is unusual to find procedures that have more than 40 cycles. Errors made by DNA polymerase can affect the extension reaction of PCR during five distinct steps: (1) the binding of the correct dNTP by polymerase; (2) the rate of phosphodiester bond formation; (3) the rate of pyrophosphate release; (4) the continuation of extension after a misincorporation; and (5) the ability of the enzyme to adjust to a misincorporated base by providing 3'-to-5' exonuclease 'proofreading' activity. Misincorporation rates for different polymerases are described in terms of errors per nucleotide polymerized, and the rate can be greatly affected by many parameters. Several studies have concluded that different thermostable DNA polymerases have error rates as high as $2.1 \times 10^{-4}$ to $1.6 \times 10^{-6}$ errors per nucleotide per extension (Table 2).

Another major drawback is that standard PCR protocols can amplify DNA sequences of 3000 base pairs (3 kb) or less. Efficient long PCR requires the use of two polymerases: a non-proofreading polymerase is the main polymerase in the reaction, and a proofreading polymerase (3' to 5' exo) is present at a lower concentration. Following the results of Cheng et al. the Tth enzyme (ABI/Perkin-Elmer) enzyme has been used as the main-component polymerase and Vent (New England Biolabs) as the fractional-component polymerase. Other combinations of proofreading and non-proofreading polymerases are difficult to employ because different activities in specific buffer systems limits which combinations of polymerases can be used. Moreover, all of the problems associated with standard PCR reactions become even more critical when attempting to amplify regions of DNA 3 kb or longer.

The current invention eliminates these problems with traditional PCR by eliminating the need for a thermal cycle and a thermostable polymerase in the amplification of a sequence of DNA embedded within a longer target DNA. The current invention replaces the thermal cycle required to anneal the primers to the flanking ends of a target template by utilizing the enzymes active during homologous recombination, more specifically during homologous pairing or D-loop formation.

In bacteriophage T4, DNA replication, as well as being initiated from specific origins of replication, is also very efficiently initiated from recombination intermediates. Therefore, the current invention is directed at a system that primes DNA replication, in a specific manner, via recombination intermediates formed at opposite ends of a target sequence embedded within a much larger sequence. This permits the reaction to be run at room temperature and therefore permits the use of a non-thermal stable polymerase. The primary advantage of employing a non-thermostable polymerase is that several polymerases have been characterized which have far superior fidelity. Moreover, the characterization of accessory factors, such as sliding clamp proteins, are known to increase the length of DNA which can be amplified to entire genomes. In addition, the utilization of enzymes to deliver the primers eliminates all of the problems associated with annealing primers within the context of a thermal cycle mentioned above. Moreover, the homologous pairing reaction catalyzed by the bacteriophage T4 proteins is extremely efficient and would eliminate the problem of mis-priming.

TABLE 1

Thermostable DNA polymerases and their sources

| DNA Polymerase | Natural or recombinant | Source |
| --- | --- | --- |
| Taq | Natural | *Thermus aquaticus* |
| Amplitaq ® | Recombinant | *T. aquaticus* |
| Amplitaq (Stoffel fragment) ® | Recombinant | *T. aquaticus* |
| Hot Tub ™ | Natural | *Thermus flavis* |
| Pyrostase ™ | Natural | *T. flavis* |
| Vent ™ | Recombinant | *Thermococcus litoralis* |
| Deep Vent ™ | Recombinant | *Pyrococcus* GB-D |
| Tth | Recombinant | *Thermus thermophilus* |
| Pfu | Natural | *Pyrococcus furiosus* |
| ULTma ™ | Recombinant | *Thermotoga maritima* |

TABLE 2

Properties of DNA polymerases used in PCR

|  | Taq/Amplitaq ® | Stoffel fragment | Vent ™ | Deep Vent ™ | Pfu | Tth | ULTma ™ |
| --- | --- | --- | --- | --- | --- | --- | --- |
| 95° C. half-life | 40 min | 80 min | 400 min | 1380 min | >120 min | 20 min | >50 min |
| 5'3' exo | + | − | − | − | − | + | − |
| 3'5' exo | − | − | + | + | + | − | + |
| Extension rate (nt/sec) | 75 | >50 | >80 | ? | 60 | >33 | ? |
| RT activity | Weak | Weak | ? | ? | ? | Yes | ? |
| Resulting ends | 3' A | 3' A | >95% blunt | >95% blunt | blunt | 3' A | blunt |
| Strand displacement | − | − | + | + | − | − | − |
| M.W. (kDa) | 94 | 61 | ? | ? | 92 | 94 | 70 |

Error Rates
1. Taq (*Thermus aquaticus*)
    $1.1 \times 10^{-4}$ base substitutions/bp [Tindall, K. R., and Kunkel, T. A. (1988) Biochemistry 27, p 6008-6013, "Fidelity of DNA synthesis by the *Thermus aquaticus* DNA polymerase."]
    $2.4 \times 10^{-5}$ frameshift mutations/bp [Tindall and Kunkel, Id.]
    $2.1 \times 10^{-4}$ errors/bp [Keohavong, P., and Thilly, W. G. (1989) Proc Natl Acad Sci USA 86(23), p 9253-9257, "Fidelity of DNA polymerases in DNA amplification."]
    $7.2 \times 10^{-5}$ errors/bp [Ling, L. L., Keohavong, P., Dias, C., and Thilly, W. G. (1991) PCR Methods Appl 1(1) p 63-69, "Optimization of the polymerase chain reaction with regard to fidelity: modified T7, Taq, and Vent DNA polymerases."]
    $8.9 \times 10^{-5}$ errors/bp [Cariello, N. F., Swenberg, J. A., and Skopek, T. R. (1991) Nucleic Acids Res 19(15), p 4193-4198, "Fidelity of *Thermococcus Litoralis* DNA Polymerase (Vent) in PCR determined by denaturing gradient gel electrophoresis."]
    $2.0 \times 10^{-5}$ errors/bp [Lundberg, K. S., Shoemaker, D. D., Adams, M. W., Short, J. M., Sorge, J. A., and Mathur, E. J. (1991) Gene 108(1), p 1-6, "High-fidelity amplification using a thermostable DNA polymerase isolated from *Pyrococcus furiosus*."]
    $1.1 \times 10^{-4}$ errors/bp [Barnes, W. M. (1992) Gene 112(1), p 29-35, "The Fidelity of Taq polymerase catalyzing PCR is improved by an N-terminal deletion."]
2. KlenTaq (*Thermus aquaticus*, N-terminal deletion mutant)
    $5.1 \times 10^{-5}$ errors/bp [Barnes, W. M. (1992) Gene 112(1), p 29-35, "The Fidelity of Taq polymerase catalyzing PCR is improved by an N-terminal deletion."]
3. Vent (*Thermococcus litoralis*)
    $2.4 \times 10^{-5}$ errors/bp [Cariello, N. F., Swenberg, J. A., and Skopek, T. R. (1991) Nucleic Acids Res 19(15), p 4193-4198, "Fidelity of *Thermococcus Litoralis* DNA Polymerase (Vent) in PCR determined by denaturing gradient gel electrophoresis."]
    $4.5 \times 10^{-5}$ errors/bp [Ling, L. L., Keohavong, P., Dias, C., and Thilly, W. G. (1991) PCR Methods Appl 1(1) p 63-69, "Optimization of the polymerase chain reaction with regard to fidelity: modified T7, Taq, and Vent DNA polymerases."]
    5.7×10-5 errors/bp [Matilla, P., Korpela, J., Tenkanen, T., and Pitkanen, K. (1991) Nucleic Acids Res 19(18), p 4967-4973, "Fidelity of DNA synthesis by the *Thermococcus litoralis* DNA polymerase—an extremely heat stable enzyme with proofreading activity."]
4. Vent(exo-) (*Thermococcus litoralis*)
    $1.9 \times 10^{-4}$ errors/bp [Matilla et al., Id.]
5. Deep Vent (*Pyrococcus* species GB-D)
    No published literature. New England Biolabs claims fidelity is equal to or greater than that of Vent.
6. Deep Vent(exo-)
    No published literature.
7. Pfu (*Pyrococcus furiosus*)
    $1.6 \times 10^{-6}$ errors/base [Lundberg, K. S., Shoemaker, D. D., Adams, M. W., Short, J. M., Sorge, J. A., and Mathur, E. J.

(1991) Gene 108(1), p 1-6, "High-fidelity amplification using a thermostable DNA polymerase isolated from *Pyrococcus furiosus*."]

8. Replinase (*Thermus flavis*)

$1.03 \times 10^{-4}$ errors/base [Matilla, P., Korpela, J., Tenkanen, T., and Pitkanen, K. (1991) Nucleic Acids Res 19(18), p 4967-4973, "Fidelity of DNA synthesis by the *Thermococcus litoralis* DNA polymerase—an extremely heat stable enzyme with proofreading activity."]

BRIEF SUMMARY OF THE INVENTION

In one aspect, the present invention contemplates a method for replicating and amplifying a target nucleic acid sequence comprising reacting a primer that is complementary to a target sequence within a nucleic acid duplex with the nucleic acid duplex in the presence of a recombination factor to form a recombination intermediate, without previously denaturing the nucleic acid duplex. The recombination intermediate so formed is then admixed with a polymerase to form a polymerase complex, whereby the polymerase replicates the target sequence. Preferably, the polymerase is a polymerase holoenzyme. More preferably, the polymerase holoenzyme comprises a polymerase enzyme, a clamp protein, and a clamp loader protein. Although other sources and materials can be used, it is preferred that the recombination factor, the polymerase, the clamp protein and clamp loader be obtained from bacteriophage T4. Thus, the recombination factor is preferably bacteriophage T4 UvsX protein, the polymerase is preferably bacteriophage T4 gene product (gp) 43 polymerase, the clamp protein is preferably bacteriophage T4 gp 45 clamp protein and the clamp loader is preferably bacteriophage T4 gp44/gp 62 clamp loader complex.

In one preferred embodiment, the primer is designed to anneal at complimentary sites flanking the target nucleic acid sequence. In a further preferred embodiment, the polymerase holoenzyme complex comprises a viral, bacteriophage, eukaryotic, archaebacterial, or prokaryotic polymerase holoenzyme complex. Preferably, the bacteriophage is T4, and the holoenzyme complex includes the gene product 43 polymerase. Preferably, the bacteriophage is T4, and the holoenzyme complex includes the gene product 45 clamp protein.

In a further aspect, a contemplated method uses a single stranded binding protein to facilitate downstream strand displacement synthesis by the polymerase holoenzyme complex. The single stranded protein is preferably gene product 32 from the T4 bacteriophage system.

In yet another aspect, a contemplated method uses a single stranded binding protein to destabilize the helix at or near the point of the primer template junction.

In a still further aspect, the present invention contemplates a method for reproducing and amplifying a target nucleic acid sequence at a temperature below about 45° Celsius and comprises catalytically inserting a primer into the target nucleic acid sequence without previously denaturing the duplex in whole or in part to form a recombination intermediate. The recombination intermediate so formed is then admixed with a polymerase to form a polymerase complex, whereby the polymerase replicates the target nucleic acid sequence. The primer is preferably pretreated with single stranded nucleic acid binding protein. It is also preferred that the primer be pretreated with a recombination factor. A preferred recombination factor is bacteriophage T4 UvsX. A preferred polymerase is gene product 43 DNA polymerase from the bacteriophage T4.

In a further aspect, an above-contemplated method uses a helicase to facilitate replication by the polymerase. A preferred helicase is bacteriophage T4 gene product 41 DNA helicase. A further preferred helicase is bacteriophage T4 replicative helicase complex, comprising bacteriophage T4 gp 41 and gp 59.

In another aspect, a contemplated method uses an accessory factor to stabilize the recombination factor. A preferred accessory factor is bacteriophage T4 UvsY. In a still further aspect, a contemplated method uses a combination of a helicase and an accessory factor. A preferred helicase is bacteriophage T4 gp41. A preferred accessory factor is bacteriophage T4 UvsY.

In yet another aspect, the present invention contemplates a method of creating a library of nucleic acid sequences. This method comprises incubating a first double-stranded nucleic acid with an enzyme with exonuclease activity to form a plurality of single stranded DNA regions having random sizes. This plurality of single stranded DNA regions is treated with a recombination factor to form a plurality of pretreated single stranded DNA regions. A second double-stranded nucleic acid is then added to the plurality of pretreated single stranded DNA regions to form a plurality of three stranded crossover junctions. The plurality of three stranded crossover junctions is incubated with a helicase to form a plurality of Holliday junctions. The plurality of Holiday junctions so formed is resolved by incubation with an endonuclease. Preferably, the recombination factor is bacteriophage T4 UvsX. Preferably, the helicase is bacteriophage T4 gene products 41 and 59. A further preferred helicase is bacteriophage T4 UvsW. A preferred endonuclease is bacteriophage T4 gp 49.

BRIEF DESCRIPTION OF THE DRAWINGS

In the drawings forming a portion of this disclosure.

DETAILED DESCRIPTION OF THE INVENTION

A. Basic Replication and Amplification Process

In one aspect, a process of the invention comprises treating a nucleic acid, such as RNA or DNA, with an oligonucleotide primer, which primer is complementary to a predetermined target sequence within that nucleic acid. Preferably, the nucleic acid is double stranded, such as in the form of a DNA heteroduplex. A process of the invention contemplates reacting separate complementary strands of a nucleic acid heteroduplex with a molar excess of two oligonucleotide primers. Significantly, this treatment does not require the prior denaturation of the complementary strands of the nucleic acid heteroduplex. Rather, the hybridization of the primer with its target sequence is mediated by a recombination factor. The recombination factor functions to form a recombination intermediate. An exemplary recombination intermediate is a D-loop structure between the primer and the complementary strands of the nucleic acid heteroduplex. The recombination factor can be used to pre-treat the primer at temperatures below 90° C., more preferably below 45° C., and most preferably at 37° C.

Figure 1:
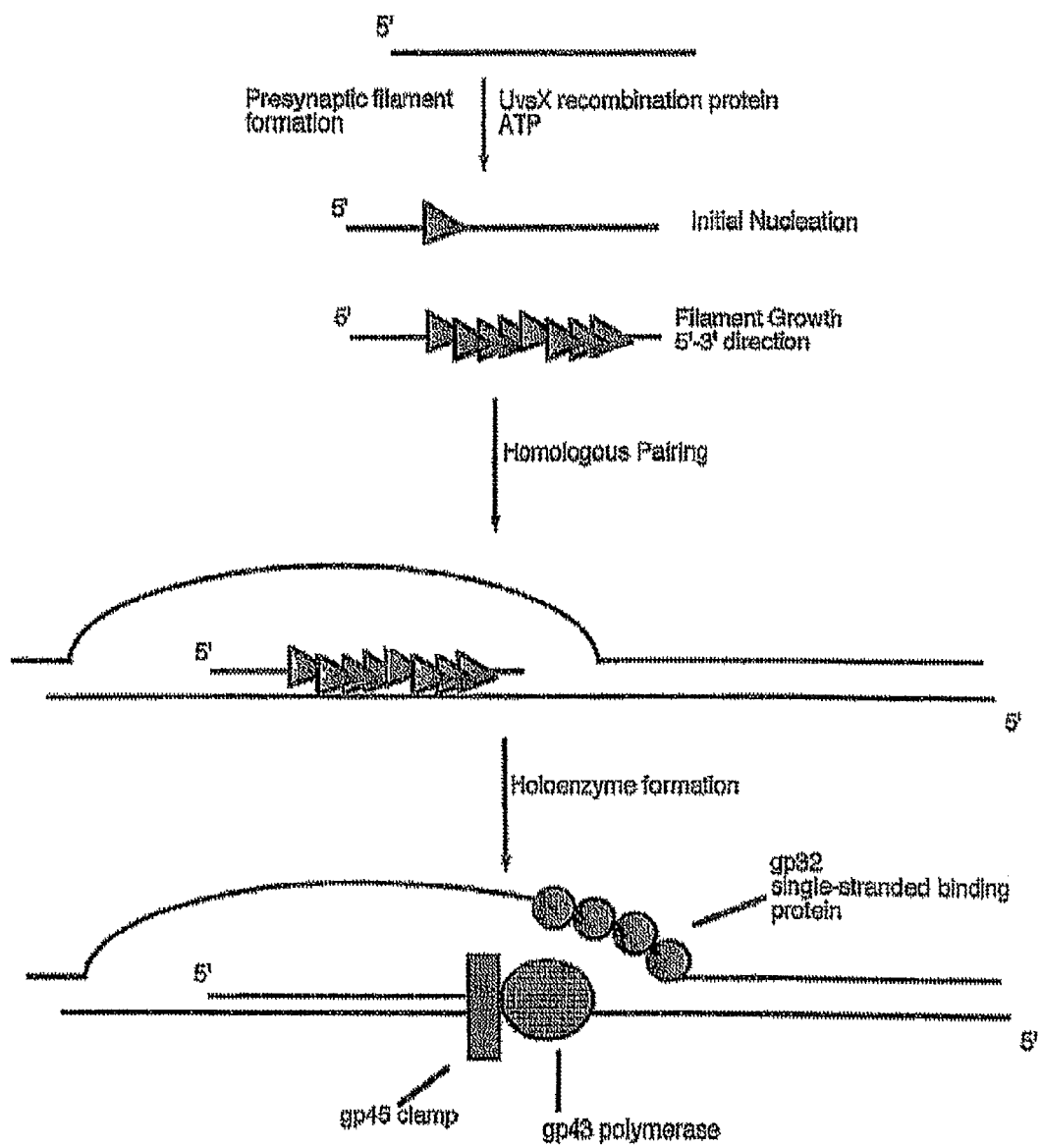
FIG. 1 depicts polymerase holoenzyme complex formation at a recombination D-loop.

A preferred recombination factor is the bacteriophage T4 UvsX gene product. A recombination factors, such as UvsX, can require additional components, such as ATP, in order to optimally function. The bacteriophage T4 UvsX protein functions to facilitate formation of a presynaptic filament capable of undergoing homologous pairing (See FIG. 1). When mixed with the target nucleic acid, the resultant recombination intermediates, positioned at opposite ends of the target nucleic acid, can serve as sites for attachment of a polymerase. A preferred polymerase is a polymerase holoenzyme. Preferably, the polymerase holoenzyme is the polymerase holoenzyme of bacteriophage T4.

Figure 2:
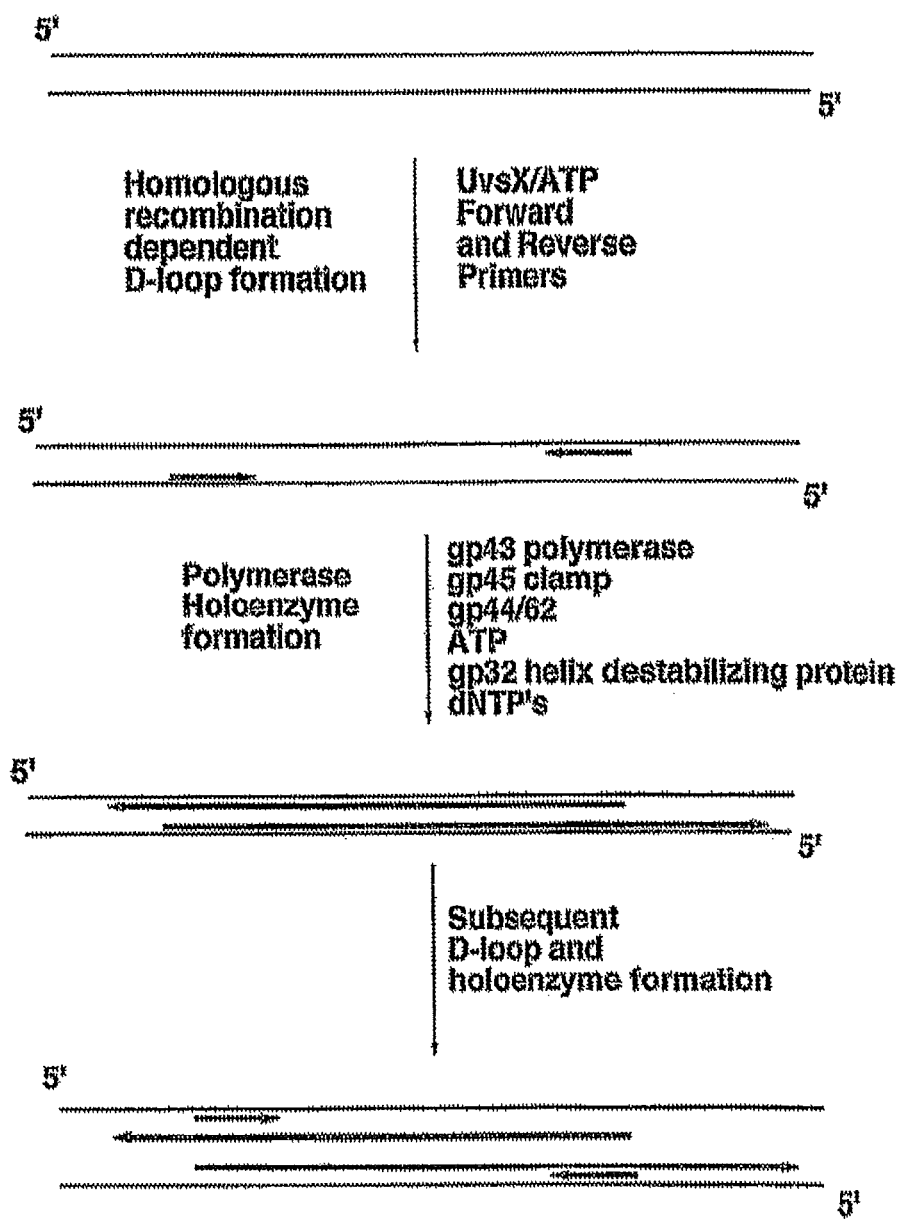
FIG. 2 depicts a gene amplification system using a method of the invention.

The formation of the bacteriophage T4 polymerase holoenzyme complex is shown in FIG. 2. This polymerase holoenzyme complex includes the gene product (gp) 43 DNA polymerase, the gene product 45 clamp protein, and the gene products 44 and 62, which together facilitate association of the gene 45 clamp with the gene product 43 polymerase explicitly at the recombination intermediate primer/template junction (See FIG. 2).

The gene product 32 single-stranded binding protein is added to facilitate strand displacement synthesis by the polymerase holoenzyme complex (See FIG. 2). The addition of accessory factors to stabilize the recombination factor is also contemplated. For example, the bacteriophage UvsY protein, a UvsX protein accessory factor, serves to stabilize the initial presynaptic filament permitting the introduction of the bacteriophage T4 replicative helicase complex, the products of the genes 41 and 59. This will constitute the assembly of an intact replication fork which can extend the range of site specific nucleic acid amplification beyond what can be expected using available thermostable polymerases alone during a thermocycle.

In some embodiments of a method of the invention, a polymerase with high fidelity and high processivity is used, namely bacteriophage T4 gp 43 DNA polymerase. This polymerase has been shown to have an accuracy in replication that is orders of magnitude greater than those polymerases commonly associated with PCR, and with the PCR technique. This polymerase has a built in proofreading/editing function which, when used in connection with a self contained DNA duplication process, significantly increases the accuracy of that duplication process.

Not only does this increase in processivity produce a more accurate duplicate, it enhances the ability of the technique to accurately replicate target nucleic acids with many thousands of base pairs. Homologous polymerase holoenzymes are found in other species, such as the DNA polymerase III found in prokaryotic systems, and DNA polymerase delta and epsilon holoenzymes in eukaryotic systems.

In other embodiments of a method of the invention, use of a holoenzyme complex, a gene clamp, and a helicase complex, enables polymerase to efficiently operate along much longer nucleic acid sequences than can predictably be duplicated with existing PCR technologies.

In a further aspect, the present invention contemplates a method for reproducing and amplifying a target nucleic acid sequence at a temperature below about 45° Celsius and comprises catalytically inserting a primer into the target nucleic acid sequence without previously denaturing the duplex in whole or in part to form a recombination intermediate. The entire duplication and amplification process can occur at temperatures below about 90° C., more preferably below about 45° C., and most preferably at about 37° C., due to the catalytic nature of the involved processes. Because no thermostable enzymes are required, the problems associated with magnesium chloride solutions and their concentrations are avoided. Similarly, the use of mineral oil is eliminated.

Because the present invention is based upon the creation of a recombination intermediate, such as a D-loop, without previously denaturing the duplex, and can be conducted at temperatures of about 37° C., it eliminates the extraneous and undesirable/nonspecific annealing that occurs along the length of the denatured duplex, and eliminates issues of having the wrong primer concentrations, programming difficulties with PCR machines, and having excessive or insufficient templates.

Avoiding these problems commonly associated with PCR further augments the capability of a process of the invention to replicate and amplify with greater fidelity and processivity.

The recombination intermediate so formed is then admixed with a polymerase to form a polymerase complex, whereby the polymerase replicates the target nucleic acid sequence. The primer is preferably pretreated with single stranded nucleic acid binding protein. It is also preferred that the primer be pretreated with a recombination factor. A preferred recombination factor is bacteriophage T4 UvsX. A preferred polymerase is gene product 43 DNA polymerase from the bacteriophage T4.

As is understood by one of ordinary skill in the art, the replication and amplification of a target nucleic acid sequence by a polymerase requires the presence of nucleotide triphosphates in concentrations sufficient to permit elongation of the nascent copies. In addition, the concentrations of the other components of a method of the invention can readily be determined by one of ordinary skill in the art, based upon empirical determinations as well as the examples that follow.

Moreover, as is well understood by one of ordinary skill in the art, a method of the present invention permits additional rounds, or cycles, of replication of a target nucleic acid sequence, by virtue of the re-initiation of a method of the invention. As such, not only is a target nucleic acid sequence copied or replicated, it is amplified as a result of the repetition of a method of the invention. While not wishing to be bound by theory, it is believed that the presence of a molar excess of a primer in embodiments of the invention permits the repeated formation of a recombination intermediate and subsequent replication of a nucleic acid target. In this sense, the present invention provides an alternative to the target amplification of PCR.

B. Use of Process to Create Libraries

In addition to specific nucleic acid amplification, a process of the invention contemplates the use of the bacteriophage T4 presynaptic filament (gene products of the UvsX, UvsY, and gp32 genes) to promote the recombination of different nucleic acid sequences to produce a protein with desired novel functional characteristics. This method comprises incubating a first double-stranded nucleic acid with an enzyme having exonuclease activity to form a plurality of single stranded DNA regions having random sizes. The exonuclease treatment is performed under conditions that would randomize the size and distribution of the resultant single stranded DNA region.

This plurality of single stranded DNA regions is treated with a recombination factor to form a plurality of pretreated single stranded DNA regions. For example, in a preferred embodiment, in the presence of the bacteriophage T4 UvsX and UvsY gene products and a second undigested target nucleic acid sequence, an initial three stranded crossover reaction occurs in a random manner as dictated by the distribution of the exonuclease digestion of the first nucleic acid upon which the presynaptic filament is formed.

A second double-stranded nucleic acid is then added to the plurality of pretreated single stranded DNA regions to form a plurality of three stranded crossover junctions. The plurality of three stranded crossover junctions is incubated with a helicase to form a plurality of Holliday junctions. The plurality of Holliday junctions so formed is resolved by incubation with an endonuclease. Preferably, the recombination factor is bacteriophage T4 UvsX. Preferably, the helicase is bacteriophage T4 gene products 41 and 59. A further preferred helicase is bacteriophage T4 UvsW. A preferred endonuclease is bacteriophage T4 gp 49.

Figure 3:
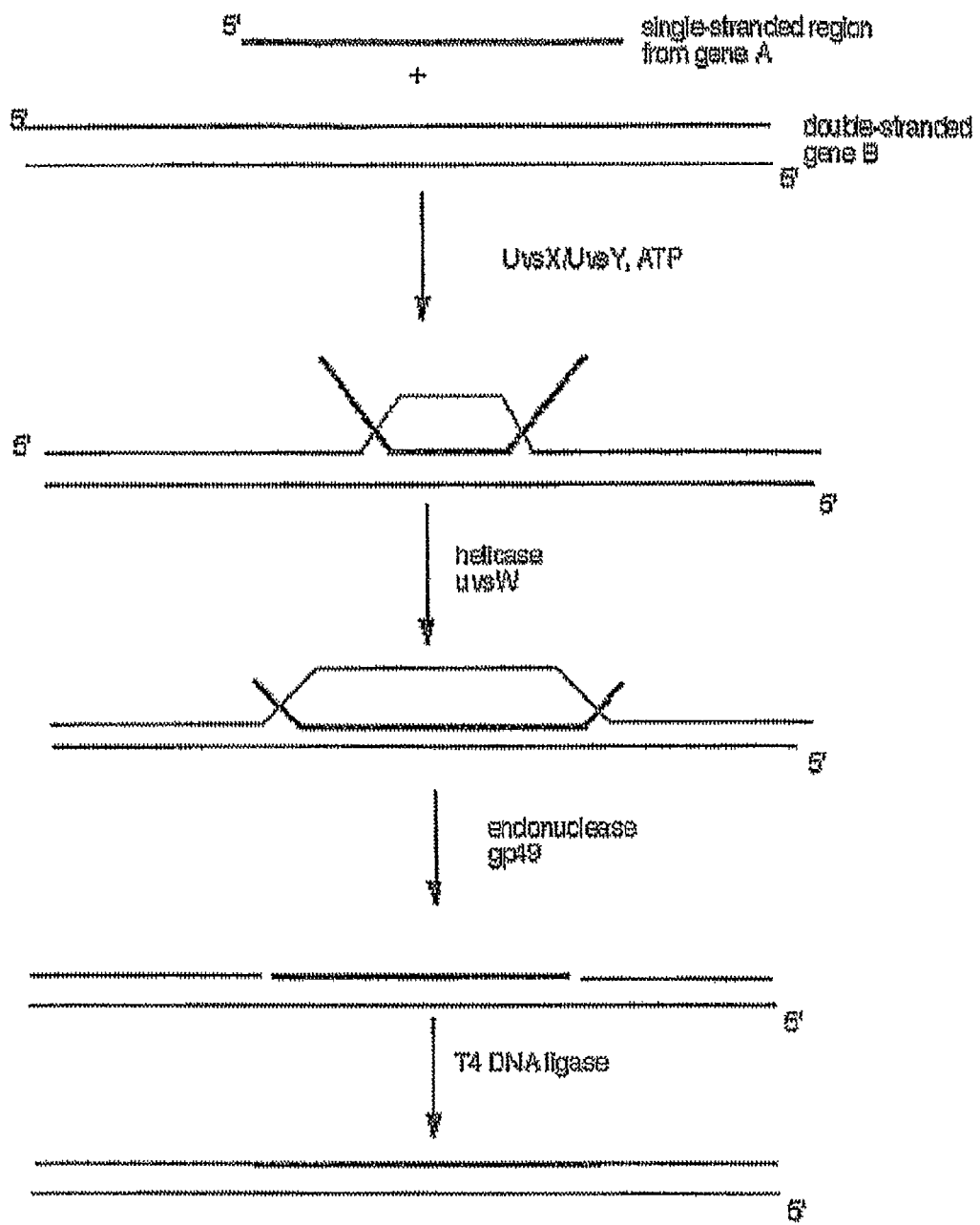
FIG. 3 depicts creation of a library of novel recombinant nucleic acid sequences using a method of the invention.

Upon addition of helicase activity derived from the products of genes 41 and 59, branch migration extends regions of heteroduplex DNA beyond regions of non- or partial homology. The final products of the reaction can be resolved with the bacteriophage gene product 49 protein, an endonuclease that will specifically recognize and cleave recombination crossover junctions (Holliday junctions) (See FIG. 3).

Enzymes from other species can be used in a contemplated method of the invention, in addition to enzymes from the bacteriophage T4 system. For example, enzymes from *E. coli*, including RecA, RecF, RecO, RecR, RuvA, RuvB, RecG, and RuvC, can be used. A recombination factor useful in some embodiments of a method of the invention includes the UvsX protein from bacteriophage T4, the RecA protein from *E. coli*, and the Rad51 protein from yeast, as well as Rad51 homologs from other eukaryotic species. An accessory factor useful in some embodiments of a method of the invention includes the UvsY protein from bacteriophage T4, the Rec F, O and R proteins from *E. coli*, and the Rad52 protein from yeast, as well as Rad52 homologs from other eukaryotic species.

In addition to the bacteriophage T4 polymerase, clamp and clamp loading complex, the DNA polymerase III holoenzyme, the beta-clamp clamp and the gamma-complex clamp loading complex from prokaryotic species can be used in a method of the invention. Still further, the DNA polymerase delta and epsilon holoenzymes, the PCNA clamp, and the replication factor C complex clamp loading complex from eukaryotic species can be used in a method of the invention.

EXAMPLES

Example 1

Homologous recombination directed nucleic acid amplification of closed circular plasmid DNA using the T4 holoenzyme complex and the T4 homologous recombination proteins UvsX and gene product 32 were performed as follows. Oligonucleotide primers were designed to amplify a 3220 base pair fragment from M13mp18 plasmid DNA as follows:

```
                                            (SEQ ID. NO. 1)
1940-5'TGATACACCTATTCCGGGCTATACTTATAT-3'
and
                                            (SEQ ID. NO. 2)
5160 5'-CGCTCAATCGTCTGAAATGGATTATTTACATTGGCAGATT-
3'.
```

These primers were used for the amplification of a 3220 base pair fragment from closed circular M13mp18 plasmid DNA. Reaction conditions were set up to facilitate the assembly of the polymerase holoenzyme, including bacteriophage T4 gene products 43, 45, and 44/62, on recombination intermediates formed by the action of bacteriophage T4 UvsX protein. The concentration of double stranded closed circular M13mp18 plasmid DNA was set at 10 micrograms per milliliter (2.1 nanomolar as nucleotides). Both oligonucleotides, 1940 (SEQ ID NO. 1) and 5160 (SEQ ID NO. 2), were used at a concentration of 210 nanomolar (as molecules). The concentration of UvsX was present to ensure about 50% coverage of the 40 mer oligonucleotide primers (UvsX monomer/4 base site size). The concentration of ATP was set at 2 millimolar during the D-loop reaction, and an ATP regeneration system was employed consisting of phosphocreatine kinase and phosphoenol pyruvate. The gene product (gp) 32 single stranded protein was present at 25 micromolar. The holoenzyme was constructed using 1micromolar gp43 (polymerase), 1 micromolar gp45 (as trimers, sliding clamp) and 500 nanomolar gp44/62 complex (ATP dependent clamp loader). The deoxyribonucleotides were present at 3 millimolar.

The reaction order was designed to allow for the initial formation of a recombination intermediate, or D-loop, followed by the formation of a polymerase holoenzyme complex. The M13mp18 closed circular double stranded DNA template was first incubated in holoenzyme complex formation buffer (20 millimolar Tris (pH7.5), 150 millimolar KOAc, 10 millimolar Mg(OAc)$_2$) in the presence of the primers, 2 millimolar ATP, phosphoenol pyruvate and pyruvate kinase.

Homologous pairing, or D-loop formation, was then initiated by the addition of the T4 UvsX strand tranferase protein. After 2 minutes at 37° C., an additional 1 millimolar ATP, 3 millimolar deoxyribonucleotide mix, gp 32 single stranded binding protein and the gp43 polymerase and the gp45 and gp44/62 accessory factors were added to initiate polymerase holoenzyme formation at recombination intermediates and initiate strand displacement DNA synthesis. At 10, 20 and 30 minutes aliquots of the reaction mix were removed and quenched with SDS and EDTA followed by heating to 60° C. for 10 minutes. The reactions were then loaded onto a 1.0% TBE agarose gel and visualized using ethidium bromide.

Example 2

Homologous recombination directed nucleic acid amplification of linear plasmid DNA using the T4 holoenzyme complex and the T4 homologous recombination proteins UvsX and gene product 32. M13mp18 double stranded closed circular plasmid DNA was made linear by digestion with the BamH1 restriction endonuclease. 10 micrograms M13mp18 and the BamH1 restriction endonuclease were incubated at 37° C. using standard buffer conditions for 2 hours followed by phenol/chloroform extraction and passage through two G-25 spin columns. Reaction conditions were as described for Example 1.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. A system for replicating a target nucleic acid sequence within a nucleic acid molecule, the system comprising:
 a reaction vessel containing a reaction mixture, wherein the reaction mixture includes:
  (a) a target nucleic acid molecule including a target nucleic acid sequence;
  (b) a UvsX recombination factor;
  (c) two primers that bind to the flanking ends of the target nucleic acid sequence;
  (d) a DNA polymerase; and
  (e) nucleotides in an amount sufficient to support replication of the target nucleic acid sequence.

2. The system according to claim 1, wherein the system further includes a detector configured to detect the product produced via replication of the target nucleic acid sequence.

3. The system according to claim 2, wherein the detector is configured to detect fluorescence.

4. The system according to claim 1 wherein said DNA polymerase is a gene product of a viral, bacteriophage, prokaryotic, or eukaryotic system.

5. The system according to claim 1 wherein said DNA polymerase is a holoenzyme complex.

6. The system according to claim 1 wherein said uvsX recombination factor is a gene product of a bacteriophage.

7. The system according to claim 1, wherein said DNA polymerase is a product of a viral, bacteriophage, prokaryotic, or eukaryotic system.

8. The system according to claim 1 wherein the reaction vessel also includes a single stranded nucleic acid binding protein.

9. The system according to claim 1 wherein the reaction vessel also includes a helicase.

10. The system according to claim 1 wherein the reaction vessel also includes an accessory factor configured to stabilize the UvsX recombination factor.

11. The system according to claim 1 wherein the reaction vessel also includes an ATP regeneration system.

12. The system according to claim 1, wherein the target nucleic acid molecule is double stranded.

13. The system according to claim 1, wherein the target nucleic acid sequence is embedded within the longer target nucleic acid molecule.

\* \* \* \* \*